United States Patent [19]

Lebron et al.

[11] Patent Number: 5,085,998
[45] Date of Patent: Feb. 4, 1992

[54] BIODEGRADATION OF 2,4,6-TRINITROTOLUENE BY WHITE-ROT FUNGUS

[75] Inventors: Carmen A. Lebron, Camarillo; Leslie A. Karr, Ventura, both of Calif.; Tudor Fernando, Logan; Steven D. Aust, North Logan, both of Utah

[73] Assignee: The United States of America as represented by the Secretary of the Navy, Washington, D.C.

[21] Appl. No.: 700,854

[22] Filed: May 7, 1991

[51] Int. Cl.$^5$ .................. C12P 1/02; C12R 1/645; C12N 1/16

[52] U.S. Cl. .................. 435/262; 435/171; 435/254; 435/911

[58] Field of Search .......... 435/171, 262, 911, 254

[56] References Cited

PUBLICATIONS

CA 13:55647(7) Fernando et al. (AEMIDF) Appl. Environ Microbiol vol. 56(6) 1666–71 (1990).
CA 96:159060(19) Naumova et al. (PBMIAK) V18(1) P8590 1982.
"Biotech Abs 91–04819 Glaser" Advan Appl. Biotech Ser (1990) pp. 267–284.
Biotech Abs. 89–08258 Joyce et al. (ACSRAL) Abstr. Pap Am Chem. Soc (1989) 197 Meeting.
"Biotech Abs. 88–09640 Change" Biotech U.S.A. 1987 (1987) 190–98.
Biotech Abs. 88–01850 Joyce et al. (ACSRAL) Abst. Pap Am Chem. Soc. (1987) 194 Meeting.

*Primary Examiner*—Herbert J. Lilling
*Attorney, Agent, or Firm*—David S. Kalmbaugh

[57] ABSTRACT

There is provided a process for biodegradation of TNT (2,4,6-Trinitrotoluene) wherein the biodegradation is done utilizing the fungus *Phanerochaete chrysosporium* strain BKM F-1767, wherein waste containing TNT is treated with the fungus under predetermined conditioning and for a time period sufficient for biodegradation to occur rendering the waste ecologically acceptable to the environment.

5 Claims, 2 Drawing Sheets

BIODEGRADATION OF 2,4,6-TRINITROTOLUENE BY WHITE-ROT FUNGUS

BACKGROUND OF THE INVENTION

1. Field of the Invention

This invention relates generally to the biological treatment of ordnance or explosives to improve the environmental character thereof and, in particular, to the degradation of TNT (2,4,6-Trinitrotoluene) by using *Phanerochaete chrysosporium* or white-rot fungus to convert TNT to $CO_2$.

2. Description of the Prior Art

The compound TNT (2,4,6-trinitrotoluene) is the predominant conventional explosive used by military forces. Unfortunately, past practices for the disposal of TNT generated during the production of TNT and of military ordnance which use TNT have led to soil, sediment, and water contamination. This is of concern because exposure to TNT can cause diseases such as pancytopenia, a disorder of the blood forming tissues characterized by a pronounced decrease in the number of leukocytes, erythrocytes and reticulocytes in the human body. In addition, TNT is known to be toxic to fish such as bluegills at concentrations of 2 to 3 micrograms per milliliter, certain green algae such as *Microcystis aeruoinosa* and oysters.

In the past TNT has been treated by methods such as the invention disclosed in U.S. Pat. No. 4,038,116 to Andrews et.al. U.S. Pat. No. 4,038,116 discloses a method for treating an aqueous solution of aromatic explosives whereby explosive molecules, such as TNT, are destroyed, and the resulting effluent is safe for disposal. An additive, such as acetone or hydrogen peroxide, is added to an aqueous solution of an aromatic explosive and this mixture is exposed to ultraviolet light. The light exposure of the additive provides a free radical which strips hydrogen molecules from the aromatic explosive to change the aromatic explosive to an unstable intermediate compound. Continued exposure of the unstable intermediate compound to ultraviolet light converts the unstable intermediate compound to carbon dioxide and ammonia. While satisfactory for its intended purpose, that of disposing of aromatic explosives such as TNT, the invention of U.S. Pat. No. 4,038,116 is not very efficient for large scale treatment of contaminated waste disposal sites, can require a considerable expenditure of funds to obtain the required materials and equipment and has obvious limitations, particularly when it is required to treat soil contaminated with TNT.

It is therefore an object of the present invention to provide a relatively inexpensive and efficient method for disposing of waste discharges containing the explosive TNT.

It is further an object of the present invention to provide an ecologically acceptable method of disposing of waste discharges containing TNT by biodegrading the TNT using white rot fungus to convert TNT to carbon dioxide ($CO_2$).

Other objects, advantages, and novel features of the present invention will become apparent from the following detailed description of the present invention.

SUMMARY OF THE INVENTION

The present invention comprises a process of biodegrading TNT contained in liquid or solid waste utilizing a white-rot fungus as the active ingredient in the TNT degrading process. The white-rot fungus is grown in a liquid medium in the presence of certain nutrients including nitrogen. The white-rot fungus is then caused to enter a secondary metabolic state by limiting the nutrient nitrogen and supplying a carbon source for hydrogen peroxide production. After the white-rot fungus enters a secondary metabolic state the white-rot fungus is capable of degrading TNT. The white-rot fungus may then be added to soil containing TNT resulting in degradation of the TNT within the soil. It has been determined that over a period of 90 days approximately 85% of TNT in water at 100 mg/liter and in soil at 10,000 mg/kg was degraded.

DETAILED DESCRIPTION OF THE PREFERRED EMBODIMENT

Though the process of the present invention can use any of many white-rot fungus, *Phanerochaete chrysosporium* strain VKM-F-1767 was used in the preferred embodiment of the present invention because of its vigorous growth and rapid degradation capabilities. The white-rot fungus, *Phanerochaete chrysosporium* strain VKM-F-1767 used to degrade TNT was acquired from the Forest Products Laboratory, U.S. Department of Agriculture, Madison, Wis. A culture of the white-rot fungus, Phanerochaete chrysosporium strain VKM F-1767, is deposited with the American Type Culture Collection, 12301 Parklawn Drive, Rockville, Md. 20852-1776. The accession number for the white-rot fungus, Phanerochaete chrysosporium strain VKM F-1767 is ATCC 20696. The white-rot fungus was maintained at room temperature on 2% (wt/vol) malt agar slants.

The first step in the method/process of the present invention is to culture the white-rot fungus to provide a readily available active ingredient capable of biodegrading TNT. Such development should take place under sterile or semisterile conditions in a stationary liquid medium containing nitrogen and sufficient nutrients for germination and rapid growth. Glucose, cellulose, and inexpensive, commercially available corn cobs or a source of cellulose work equally well as a source of nutritional requirements for fungal growth.

The white-rot fungus was incubated in a liquid culture media composed of 56 millimolers (mM) glucose, 1.2 mM ammonium tartrate (nitrogen-limited), trace metals and thiamine (1 milligram per Liter) in a 20 mM 2,2'-dimethylsuccinate buffer (Ph 4.2). The liquid culture media was first sterilized by filtration through a cellulose acetate membrane filter (pore size 0.22 μm). Culture bottles for the liquid culture media were sterilized by autoclaving at 121° C. and 15 psi for 20 minutes.

Nine milliliter aliquots of the liquid culture medium were next dispensed into each of a plurality of 250 milliliter Wheaton bottles equipped with a gas exchange manifold having a Teflon seal. To grow the fungus, a one milliliter (ml), 0.5 absorbance unit at 650 nanometers spore suspension of *Phanerochaete chrysosporium* was inoculated into the liquid culture medium and grown at 39° C. The spores which readily germinate were grown in the culture medium under ambient air for 6 days. After the white-rot fungus has entered a secondary metabolic state the white-rot fungus is capable of degrading TNT. Control cultures contained the culture media minus the *Phanerochaete chrysosporium* inoculum.

At this time it should be noted that there are other processes for growing white-rot fungus, *Phanerochaete chrysosporium* strain VKM F-1767, such as the process described in Chang et. al. U.S. Pat. No. 4,554,075.

Figure 1:
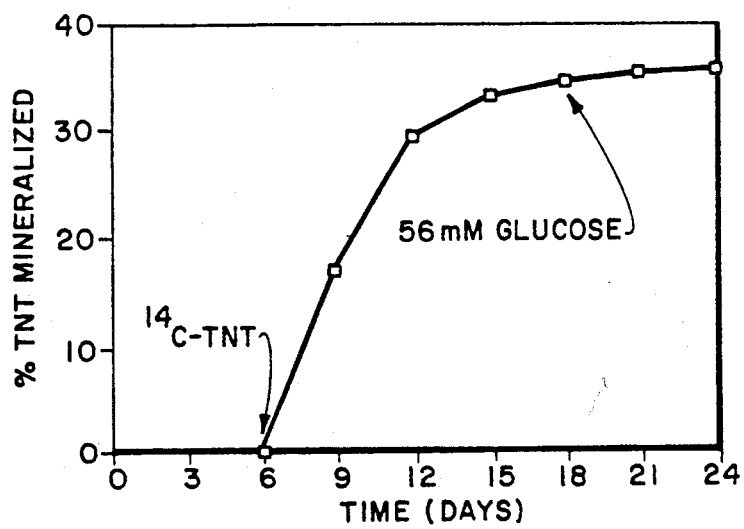
FIG. 1 is a graph illustrating the mineralization of [$^{14}C$] TNT in nutrient nitrogen-limited-liquid cultures of *Phanerochaete chrysosporium* with each culture containing 57.92 nmol of [$^{14}C$]TNT.

In one experiment, 57.92 nano-moles (13μg) of [$^{14}$C]TNT, which is a radiolabeled or radioactive TNT having a specific activity of 21.58 Mci/nmol, was added to the nitrogen limited cultures after six days of the white-rot fungus growth under ambient atmosphere. At 3-day intervals thereafter, the headspaces of the culture bottles were flushed with oxygen (99.9% pure) and liberated $CO_2$ was passed through a volatile organic trap consisting of 10 ml of scintillation cocktail, tradename Safety Solve, manufactured by Research Products International Corp. of Mt. Prospect, Ill. prior to passage through a vial containing 10 ml of $CO_2$ trap. The $CO_2$ trap was a mixture of ethanolamine in methanol and scintillation cocktail (1:4:5; vol/vol/vol). The volatile organic trap was used to ensure that the radiolabeled material trapped in the $CO_2$ trap was not contaminated with volatile organics as a result of air stripping during flushing. The amount of radioactivity in each trap was then determined by liquid scintillation spectrometry and is best illustrated by FIG. 1. It should be noted that the radiolabeled TNT was manufactured by Chemsyn Science Laboratories of Lenexa, Kans.

The ability of white-rot fungus to degrade [$^{14}$C]TNT in soil was also examined in a second experiment. An agricultural silt loam soil consisting of 19% sand, 54% silt and 27% clay was used in this experiment. The organic matter content of the soil was 3.62% of which 2.10% was organic carbon. Total nitrogen was 0.19% and the soil Ph was 6.4. The cation exchange capacity was 23.6 milliequivalents per 100 grams. Ten grams of soil was placed in 250 ml Wheaton bottles. Then, 57.92 nmoles of [$^{14}$C]TNT dissolved in 160 μl acetone was added to the soil. The acetone was allowed to evaporate and the soil was then mixed with 6.7 grams of corn cob that had ten days earlier been inoculated with white-rot fungus. The moisture content of the soil was adjusted to the maximum water binding capacity of the mixture by adding 3.5 ml of water. Unlike the liquid culture experiment, sterile conditions were not used. Also, cultures were not supplemented with buffer, trace metals or other nutrients. Cultures were incubated at 39° C. for 30 days. Every 3 days the head spaces of the culture bottles were flushed with oxygen. The liberated $^{14}CO_2$ was trapped in the manner described for the first experiment, and the amount of $^{14}CO_2$ recovered was determined by liquid scintillation spectrometry. The results of the second experiment are, in turn, illustrated by FIG. 2.

To perform mass balance analyses on liquid cultures incubated with [$^{14}$C]TNT, the contents of each 250 ml Wheaton bottle were extracted three times with 30 ml of dichloromethane and 30 ml of water (1:1, vol/vol). The dichloromethane extracts were combined and concentrated by evaporation under a gentle stream of nitrogen. Following the extractions, particulate matter, that is fungal mat, was separated from the aqueous fraction by filtration through glass wool. The amount of $^{14}$C which was bound to the fungal mat and not extractable by organic solvent was determined by combustion in a Harvey Biological Oxidizer manufactured by R. J. Harvey Instrument Corp. of Hillsdale, N.J. followed by measurement of trapped $^{14}CO_2$ by liquid scintillation spectrometry. The aqueous portion was also assayed for radioactivity by liquid scintillation spectrometry.

Figure 3:
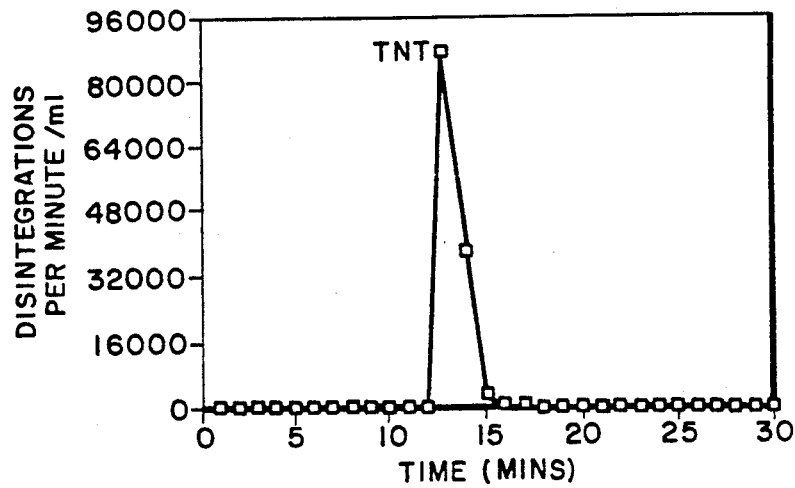
FIG. 3 is an HPLC elution profile of authentic [$^{14}C$] trinitrotoluene.

High Performance Liquid Chromatography (HPLC) of [$^{14}$C]TNT metabolites was performed by using a system equipped with a Spectra-Physics model SP 8810 pump manufactured by Spectra Physics of San Jose, Calif.; a Rheodyne injector manufactured by Rheodyne Inc. of Cotati, Calif.; a 5 μm, 4.6 by 250 mm model Rsil C-18 reverse-phase column manufactured by Beckman Instrument Inc. of San Ramon, Calif. and a Spectra-Physics model SP 8450 variable wavelength absorbance detector. Isocratic elution was performed with methanol:water (50:50 vol/vol) at a flow rate of 1 ml/min. The wavelength of the absorbance detector was 254 nm. The retention time of [$^{14}$C]TNT was established by monitoring the elution of authentic TNT at 254 nm as is best illustrated by FIG. 3. For the mass balance studies, 20 μl samples of the concentrated organic extract were used for injection into the HPLC system. One milliliter fractions were collected in scintillation vials. Nine milliliters of Safety Solve were added to each fraction, and was measured by liquid scintillation spectrometry measured the radioactivity.

Figure 4:
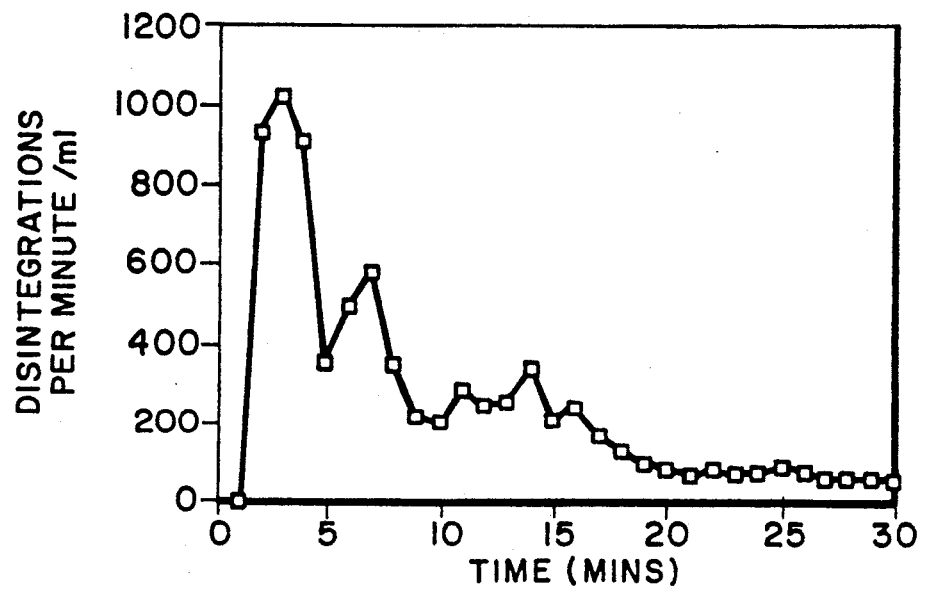
FIG. 4 is an HPLC elution profile of a methylene chloride extract of a nutrient nitrogen-limited culture of *Phanerochaete chrysosporium* incubated with [$^{14}C$]TNT for a time period of 18 days.

The results of the HPLC analysis of TNT being biodegraded by white-rot fungus in liquid cultures is illustrated in FIG. 4. FIG. 4 is an HPLC profile of methylene chloride extract of nutrient nitrogen limited culture of *Phanerochaete chrysosporium* BKM strain VKM F-1767 incubated with [$^{14}$C]TNT for 18 days. Each culture consisted of 57.9 nmol of [$^{14}$C]TNT.

At the end of a 30 day incubation period a mass balance analysis was also performed on soil cultures using extraction procedures fully described in a publication entitled "Development of an Analytical Method for Explosive Residues in Soil", by T. F. Jenkins and M. E. Walsh, Report 87-7 Cold Regions Research and Engineering Laboratory, U.S. Printing Office, Springfield, Va. The contents of each 250 ml Wheaton bottle were extracted three times with 30 ml of acetonitrile. First, the soil/corn cob mixture was dispersed using a vortex mixer for a time period of 10 minutes and followed by sonication in an ultrasonic bath for 18 hours. The acetonitrile extracts were next combined and concentrated by evaporation under a gentle stream of nitrogen. The concentrated extract was then centrifuged for 5 minutes at 1500 rpm and a ten milliliter clear supernatant was removed using a volumetric pipet and mixed with an equal volume of water in a glass scintillation vial. The contents of the vial were thoroughly mixed, allowed to stand for 15 minutes and filtered through a 0.45 μm ARCO LS-25 disposable filter assembly. The filtrate- /organic extract was collected and saved for HPLC analysis. Twenty microliters of the extract was used for HPLC analysis as described above. Metabolite formation in soil from [$^{14}$C]TNT was monitored by liquid scintillation spectrometry of the HPLC fractions. Fractions (1 ml) were collected and radioactivity was determined in the same manner as set forth for the liquid cultures. Radiolabeled compounds which were found to the soil/corn cob matrix and were not recovered by organic solvent extraction were combusted to $CO_2$ in a Biological Oxidizer and radioactivity was measured by liquid scintillation spectrometry. The vortex mixer utilized the during the extraction procedure was a model Genie 2 manufactured by Scientific Industry, Inc. of Bohemia N.Y.; the ultrasonic bath was manufactured by Branson Equipment Company of Shelton, Conn.; the biological oxidizer was manufactured by R. J. Harvey Instrument Corporation and the filter assembly was manufactured by Gelman Sciences.

Figure 5:
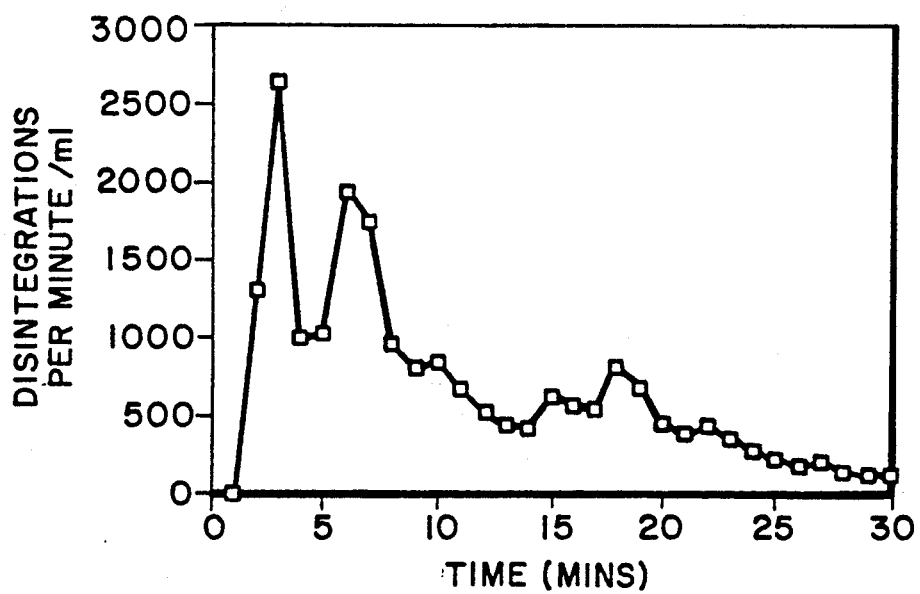
FIG. 5 is an HPLC elution profile of an acetonitrile extract of a soil-corncob culture incubated with *Phanerochaete chrysosporium* and [$^{14}C$]TNT for a time period of 30 days.

The results of the HPLC analysis of TNT being biodegraded by white-rot fungus in soil cultures are illustrated in FIG. 5. FIG. 5 is an HPLC profile of an acetonitrile extract of a soil-corncob culture incubated with *Phanerochaete chrysosporium* strain BKM-F-1767 and [$^{14}$C]TNT for a time period of 30 days. Each culture contained 57.9 nmol of [$^{14}$C]TNT.

In other experiments, white-rot fungus/*Phanerochaete chrysosporium* strain VFM-F-1767 was tested for its ability to mineralize radiolabeled TNT in both liquid and soil at levels that may be encountered in environment, i.e., 100 mg/liter in water and 10,000 mg/kg in soil. Culture conditions were as the conditions for the first and second experiments except for the concentration of TNT and the time of incubation. Rates of mineralization were obtained and mass balance analyses were performed as described for the first and second experiment after time periods of 30, 60 and 90 days for the liquid and soil cultures. One culture was extracted at each time except for the 90 day time period for soil cultures, for which two cultures were used.

The results for mass balance analysis of TNT by white-rot fungus in liquid cultures (100 mg/liter) and soil cultures (10,000 mg/kg) are set out respectively in Tables I and II.

TABLE I

Mass balances for 2,4,6-trinitrotoluene metabolism by *Phanerochaete chrysosporium* in liquid culture (100 mg/liter)

| Incubation Period (Days) | % Mineralized | % Metabolites in water fraction | % Extracted methylene chloride[a] fraction |
|---|---|---|---|
| 30 | 18.4 ± 2.4 | 52.0 | 12.1 |
| 60 | 19.0 ± 3.0 | 51.6 | 19.5 |
| 90 | 19.6 ± 3.5 | 50.1 | 22.7 |

| Incubation Period (Days) | % Adsorbed to fungal mat fraction | % Mass Recovery | % TNT Remaining |
|---|---|---|---|
| 30 | 11.0 | 93.5 | 22.1 |
| 60 | 5.1 | 95.2 | 14.9 |
| 90 | 2.2 | 94.6 | 12.3 |

[a]In liquid cultures, 6-day-old ligninoytic cultures of *P. chrysosporium* contained 57.9 nmol of [$^{14}$C]TNT and 1 mg of TNT. Mass balances were quantitated as described in Materials and Methods.

TABLE II

Mass balance for 2,4,6-trinitrotolene metabolism by *Phanerochaete chrysosporium* in soil (10,000 mg/kg)

| Period (Days) | % Mineralized | % Absorbed Extracted in acetonitrile[b] | % to soil-corncob[b] |
|---|---|---|---|
| 30 | 9.8 ± 1.9 | 69.5 | 14.4 |
| 60 | 17.1 ± 2.2 | 59.8 | 15.3 |
| 90 | 18.4 ± 2.9 | 62.6 | 11.5 |

| Incubation Period (Days) | % Mass Recovery | % TNT Remaining |
|---|---|---|
| 30 | 93.7 | 50.8 |
| 60 | 92.2 | 29.3 |
| 90 | 92.5 | 14.9 |

[a]In soil cultures, 57.9 nmol of [$^{14}$C]TNT and 100 mg of TNT, dissolved in acetone, were adsorbed onto 10 g of nonsterile soil. The acetone solvent was allowed to evaporate, 6.7 g of preinoculated corncobs was added, and the water content was adjusted to 40% (wt/wt). Mass balances were quantitated as described in Materials and Methods.

EXPERIMENTAL RESULTS

FIG. 1 shows that *Phanerochaete chrysosporium* strain VKM-F-1767 mineralized or biodegraded 35% of the [$^{14}$C]TNT to $^{14}CO_2$ during the first twelve days of incubation in a liquid culture. Supplemental glucose equivalent to 56 Mm was added to the cultures on day 18 and did not affect the evolution of $^{14}CO_2$. The liquid culture experiment was discontinued after 24 days of incubation and a mass balance analysis was performed. A total of 35.4 ±3.6% of the total radioactivity was evolved as $^{14}CO_2$, 25.1% was present as water-soluble metabolites, 15.7% was found in the methylene chloride fraction, and 17.3% was associated with the mycelial fraction. A total mass recovery of 93.5% was achieved. HPLC analysis, FIG. 4, of the methylene chloride extract demonstrated that only about 3.3% of the [$^{14}$C]TNT initially present might be identified as undegraded TNT. The remaining 12.4% represented unidentified metabolites formed during the 18-day incubation period. Almost all of the unidentified metabolites remaining in the methylene chloride extract were more polar than TNT. None of the metabolites corresponded to mono- or dinitrotoluenes. In control cultures incubated under the same culture conditions but not inoculated with *Phanerochaete chrysosporium* strain VKM-F-1767, 98% of the radioactivity was found in the methylene chloride fraction and was unmetabolized [$^{14}$C]TNT.

Figure 2:
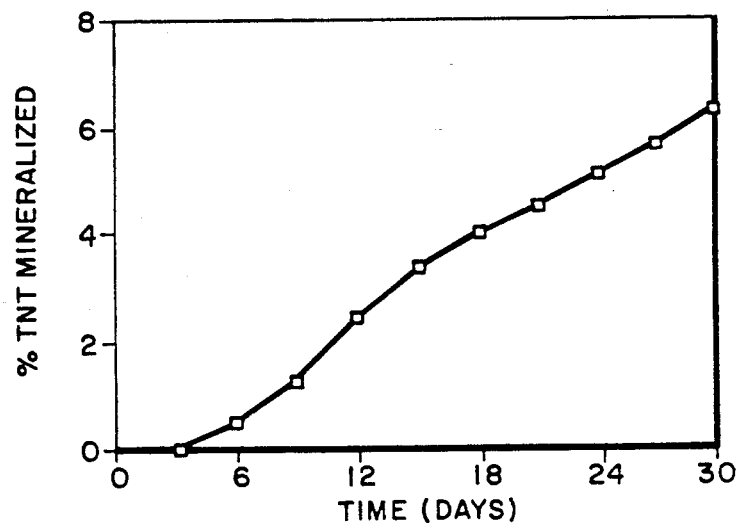
FIG. 2 is a graph illustrating the mineralization of [$^{14}C$]TNT in soil-corncob cultures of *Phanerochaete chrysosporium* with each culture consisting of 57.9 nmol of [$^{14}C$]TNT.

Biodegradation was also examined in a system in which [$^{14}$C]TNT was adsorbed into soil and mixed with corncobs previously inoculated with *Phanerochaete chrysosporium* strain VKM-F-1767. In this soil-corncob mixture, 6.3% ±0.6% of the recovered radioactivity was evolved as $^{14}CO_2$ during 30 days as is best illustrated by FIG. 2. Mass balance analysis of cultures of *Phanerochaete chrysosporium* strain VKM-F-1767 incubated with [$^{14}$C]TNT in a soil-corncob matrix for 30 days revealed that 6.3±0.6% of the recovered radioactivity was evolved as $^{14}CO_2$, 63.6% was present in the acetonitrile extract, and 25.2% was unextractable and was present in the soil-corncob matrix. This material could not be identified as it could not be extracted from the matrix. A total mass recovery of 95.1% was achieved. HPLC analysis, FIG. 5, of the radiolabeled material in the acetonitrile extract revealed that only about 2.2% of the [$^{14}$C]TNT initially present might be identified as undegraded TNT.

At the end of 30, 60, and 90 days, liquid and soil cultures contaminated with 100 mg of TNT per liter and 10,000 mg of TNT per kg, respectively, were extracted and mass balance analyses were performed. As set forth in Table I, the results of mass balance analysis of 100 milligrams of TNT per liter of contaminated liquid cultures showed that 19.6±35% of the recovered radioactivity was evolved as $^{14}CO_2$, 22.7% was found in the methylene chloride extract, 50.1% was present as water-soluble compounds, and 2.2% was bound to the fungal mat after a period of 90 days of incubation. A total mass recovery of 94.6% was achieved. When the methylene chloride fraction was analyzed by HPLC, the amounts of unmetabolized [$^{14}C$]TNT remaining in liquid cultures were 22.1%, 14.9% and 12.3% over a period of 30, 60, and 90 days of incubation, respectively. In control cultures, which were incubated under the same conditions but which were not inoculated with *Phanerochaete chrysosporium* strain BKM-F-1767, greater than 99% of the radioactivity was found in the methylene chloride extract and was identified as TNT by HPLC.

As set forth in Table II, the results of mass balance analysis of soil cultures contaminated with 10,000 milligrams of TNT per kilograms showed that 18.4%±2.9% was evolved as $^{14}CO_2$, 62.6% was found in the acetonitrile extract, and 11.5% was bound to the soil-corncob-fungal matrix after 90 days. The total mass recovery was 92.5% after a period of 90 days of incubation. When the acetonitrile extracts of the 30, 60, and 90 day cultures were analyzed by HPLC, the extracts showed that the amounts of residual [$^{14}C$]TNT that was not degraded to $^{14}CO_2$ or intermediates were 50.8%, 29.3%, and 14.9%, respectively. In control cultures incubated under the same nonsterile conditions but not inoculated with *Phanerochaete chrysosporium*, greater than 99% of the radioactivity was found in the acetonitrile fraction and was unmetabolized [$^{14}C$]TNT. The assay for radioactivity in the volatile organic trap revealed that less than 0.5% of the [$^{14}C$]TNT was volatilized or air stripped during the flushing of the cultures with oxygen. From the foregoing description, it may readily be seen that the present invention comprises a new, unique and exceeding useful process for biodegrading TNT by using white-rot fungus, which constitutes a considerable improvement over the known prior art. Obviously many modifications and variations of the present invention are possible in light of the above teachings. It is, therefore to be understood that within the scope of the appended claims the invention may be practiced otherwise than as specifically described.

What is claimed is:

1. A process of biodegrading 2,4,6-Trinitrotoluene contained in a liquid to improve the environmental characteristics thereof comprising the steps of:
   (a) providing in a liquid culture medium a white-rot fungus, Phanerochaete chrysosporium strain VKM F-1767 which is in a secondary metabolic state;
   (b) biodegrading the 2,4,6-Trinitrotoluene in the liquid by immersing the 2,4,6-Trinitrotoluene in the liquid culture medium for a sufficient time period to allow the white rot fungus, *Phanerochaete chrysosporium* strain VKM F-1767 to degrade the 2,4,6-Trinitrotoluene, while at least at a predetermined time interval exposing the fungus to oxygen.

2. The process of claim 1 wherein said predetermined time interval for exposing the fungus to oxygen is at least every three days.

3. A process of biodegrading 2,4,6-Trinitrotoluene contained in a liquid to improve the environmental characteristics thereof comprising the steps of:
   (a) growing a white-rot fungus, *Phanerochaete chyrsosporium* strain VKM F-1767 in a liquid culture medium in the presence of certain nutrients including nitrogen;
   (b) causing the white-rot fungus to enter a secondary metabolic state by limiting the nutrient nitrogen and providing a carbon source for hydrogen peroxide production;
   (c) biodegrading 2,4,6-Trinitrotoluene by adding the 2,4,6-Trinitrotoluene to the liquid culture medium for a sufficient time period for the white-rot fungus to convert the 2,4,6-Trinitrotoluene to carbon dioxide, while at least at three day intervals exposing the white-rot fungus to oxygen.

4. A process of biodegrading 2,4,6-Trinitrotoluene contained in soil to improve the environmental characteristics thereof comprising the steps of:
   (a) inoculating a nutrient containing nitrogen with a white-rot fungus, *Phanerochaete chrysosporium* strain VKM F-1767; the white-rot fungus is then caused to enter a secondary metabolic state by limiting the nutrient nitrogen and supplying a carbon source for hydrogen peroxide production;
   (b) mixing the inoculated nutrient with the soil having 2,4,6-Trinitortoluene contained therein; and
   (c) degrading 2,4,6-Trinitrotoluene contained in the soil by exposing the 2,4,6-Trinitrotoluene to said white-rot fungus, *Phanerochaete chrysosporium* strain VKM F-1767 for a time period sufficient to allow for such degradation.

5. The process of claim 4 wherein said nutrient comprises corncobs.

* * * * *